(12) United States Patent
Bonvallet et al.

(10) Patent No.: US 11,806,423 B2
(45) Date of Patent: Nov. 7, 2023

(54) COSMETIC COMPOSITIONS PROVIDING AN OCCLUSIVE TEXTURE

(71) Applicant: L'OREAL, Paris (FR)

(72) Inventors: Paul Pierre Bonvallet, Westfield, NJ (US); Susan Halpern Chirch, Basking Ridge, NJ (US); Zachary Maron, Jersey City, NJ (US); Lilian Lam Josephson, Saint Paul, MN (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/001,968

(22) Filed: Jun. 7, 2018

(65) Prior Publication Data

US 2019/0374458 A1    Dec. 12, 2019

(51) Int. Cl.
| | | |
|---|---|---|
| *A61K 8/891* | (2006.01) | |
| *A61K 8/06* | (2006.01) | |
| *A61K 8/34* | (2006.01) | |

(52) U.S. Cl.
CPC .............. *A61K 8/891* (2013.01); *A61K 8/064* (2013.01); *A61K 8/345* (2013.01)

(58) Field of Classification Search
CPC ........ A61K 8/891; A61K 8/064; A61K 8/345; A61K 8/892; A61K 8/89; A61K 8/894; A61K 8/895; A61Q 19/007; A61Q 17/00; A61P 17/16
See application file for complete search history.

(56) References Cited

U.S. PATENT DOCUMENTS

| | | | |
|---|---|---|---|
| 9,028,804 B2 | 5/2015 | Nguyen et al. | |
| 9,034,833 B1 | 5/2015 | Chiou et al. | |
| 9,549,894 B2 | 1/2017 | Chiou | |
| 2007/0128137 A1 | 6/2007 | Yoshimi et al. | |
| 2007/0196291 A1 | 8/2007 | Sakuta | |
| 2009/0246159 A1* | 10/2009 | Bui .................. A61K 8/585 | |
| | | | 424/64 |
| 2011/0256077 A1 | 10/2011 | Hayakawa | |
| 2013/0345315 A1 | 12/2013 | Chiou | |
| 2013/0345317 A1 | 12/2013 | Chiou | |
| 2016/0220455 A1 | 8/2016 | Chiou et al. | |
| 2016/0367448 A1 | 12/2016 | Youssef et al. | |
| 2019/0388306 A1* | 12/2019 | Ravni .............. A61K 8/0229 | |

FOREIGN PATENT DOCUMENTS

| | | |
|---|---|---|
| CN | 102218022 A | 10/2011 |
| CN | 105188644 A | 12/2015 |
| CN | 108025196 A | 5/2018 |
| EP | 1704853 A2 | 9/2006 |
| EP | 2377512 A2 | 10/2011 |
| EP | 2997956 A1 | 3/2016 |

OTHER PUBLICATIONS

International Search Report for counterpart Application No. PCT/US2019/035115, dated Sep. 13, 2019.

* cited by examiner

*Primary Examiner* — Robert S Cabral

(74) *Attorney, Agent, or Firm* — Laetitia Leproust; Robert Klemz

(57) ABSTRACT

A water-in-silicone cosmetic composition in the form of an emulsion. The cosmetic composition comprises an aqueous phase and a silicone phase. The aqueous phase comprises a hydrating agent from about 1% to about 40% by weight based on the total weight of the composition. The silicone phase having about 18% to about 40% of silicone-containing compounds by weight based on the total weight of the composition, comprises at least one silicone polymer; a film former from about 0.01% to about 4% by weight based on the total weight of the composition; at least one emulsifying crosslinked siloxane elastomer; at least one co-emulsifier from about 0.1% to about 3% by weight based on the total weight of the composition; and wherein the cosmetic composition has a unique occlusive texture that provides low friction and high glide.

20 Claims, No Drawings

COSMETIC COMPOSITIONS PROVIDING AN OCCLUSIVE TEXTURE

FIELD OF THE DISCLOSURE

The present disclosure relates to a cosmetic composition. More specifically, the present disclosure is directed to a water-in-silicone cosmetic composition in the form of an emulsion having a unique occlusive texture that provides low friction and high glide.

BACKGROUND

A variety of compositions, especially cosmetic compositions, have been developed to provide occlusive, transformative skin texture. Unfortunately, many of these compositions are in fact difficult to apply and do not possess a smooth feel upon application.

Although glycerin is a fairly low cost humectant or hydrating agent, problems arise when incorporating high levels of glycerin in cosmetic compositions. Incorporating high levels of glycerin, generally greater than 5%, results in a cosmetic compositions having a tacky and sticky feel upon application to skin. The tacky or oily feel is undesirable to consumers. Several approaches, such as using light emollients, powders, or combinations thereof may reduce tackiness; however, the resulting cosmetic compositions may not provide sufficient consumer appeal and may still have residual tackiness that can be felt on the skin after application.

It is an object of the present disclosure to provide a cosmetic application that provides low friction and high glide. Yet another object of the present disclosure is to provide a favorable environment for skin hydration or skin healing/repair and compatibility with makeup.

SUMMARY OF THE DISCLOSURE

The instant disclosure relates to water-in-silicone cosmetic compositions in the form of an emulsion, the composition comprising:
A) an aqueous phase comprising:
  a) a hydrating agent from about 1% to about 40% by weight based on the total weight of the composition; and
  b) from about 40% to about 80% of water by weight based on the total weight of the composition;
B) a silicone phase having from about 18% to about 40% of silicone-containing compounds by weight based on the total weight of the composition, the silicone phase comprising:
  a) at least one silicone polymer;
  b) a film former from about 0.01% to about 4% by weight based on the total weight of the composition;
  c) at least one emulsifying crosslinked siloxane elastomer;
  d) at least one co-emulsifier from about 0.1% to about 3% by weight based on the total weight of the composition;
  e) and
wherein the cosmetic composition has a surprising occlusive texture that provides low friction and high glide.

In one or more embodiments, the hydrating agent is glycerin. In some embodiments, the hydrating agent is from about 5% to about 35% by weight based on the total weight of the composition.

In some embodiments, the at least one silicone polymer is selected from the group consisting of dimethicone, a mixture of dimethicone and dimethiconol, decamethylcyclopentasiloxane, cyclomethicone, and combinations thereof. In one or more embodiments, the at least one silicone polymer is from about 0.01% to about 20% by weight based on the total weight of the composition. In some embodiments, the at least one silicone polymer is from about 0.1% to about 15% by weight based on the total weight of the composition.

In some embodiments, the film former is selected from the group consisting of Trimethylsiloxysilicate (and) polypropylsilsesquioxane, Acrylates/Polytrimethylsiloxymethacrylate Copolymer, Dimethicone (and) Acrylates/dimethicone copolymer, Polypropylsilsesquioxane, Trimethylsiloxysilicate), Crotonic acid/vinyl C8-12, Isoalkyl Esters/Va/Bis-Vinyldimethicone Crosspolymer. In one or more embodiments, the film former is from about 0.2% to about 3% by weight based on the total weight of the composition. In one embodiment, the film former is from about 0.3% to about 2% by weight based on the total weight of the composition.

In some embodiments, the at least one emulsifying crosslinked siloxane elastomer comprises a substituted or unsubstituted dimethicone/copolyol crosspolymer. In some embodiments, the at least one emulsifying crosslinked siloxane elastomer is selected from dimethicone (and) dimethicone/vinyldimethicone crosspolymer, dimethicone (and) dimethicone/PEG-10/15 crosspolymer. In one or more embodiments, the at least one emulsifying crosslinked siloxane elastomer is dimethicone/PEG-10/15 crosspolymer. In some embodiments, the emulsifying crosslinked siloxane elastomer comprises a substituted or unsubstituted dimethicone/polyglyceral crosspolymer. In one embodiment, the emulsifying crosslinked siloxane elastomer is dimethicone/polyglycerine-3 crosspolymer.

In some embodiments, the at least one co-emulsifier is selected from polyether substituted linear and branched polysiloxane copolymers. In some embodiments, the at least one co-emulsifier is selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone, dimethicone (and) dimethicone/PEG-10/15 crosspolymer PEG/PPG-18/18 dimethicone, dimethicone/dimethicone crosspolymer, dimethicone (and) dimethicone/polyglycerin-3 crosspolymer and combinations thereof. In one embodiment, the at least one co-emulsifier is lauryl Peg-9 Polydimethylsiloxyethyldimethicone.

In some embodiments, the at least one co-emulsifier is present in an amount from about 0.01% to about 12% by weight based on the total weight of the composition.

In one embodiment, the silicone-containing compounds are present from about 20% to about 35% by weight based on the total weight of the composition.

In some embodiments, the water-in-silicone cosmetic compositions further comprise one or more additional components selected from the group consisting of actives selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

In some embodiments, the water-in-silicone cosmetic compositions further comprise one or more actives selected from the group consisting of sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-dit-butyl hydroxydrocinnamate, n-hydroxysuccinimide, palmitoyl oligopeptide, chrysin, palmitoyl tetrapeptide-7, yeast extract, citric acid and combinations thereof.

Another aspect of the instant disclosure can include a water-in-silicone cosmetic composition in the form of an emulsion, the composition comprising:

A) an aqueous phase comprising:
  a) a hydrating agent from about 5% to about 35% by weight based on the total weight of the composition; and
  b) water from about 50% to about 70% by weight based on the total weight of the composition;

B) a silicone phase having from about 20% to about 38% of silicone-containing compounds by weight based on the total weight of the composition, the silicone phase comprising:
  a) at least one silicone polymer from about 0.01% to about 20% by weight based on the total weight of the composition;
  b) a film former from about 0.2% to about 3% by weight based on the total weight of the composition;
  c) at least one emulsifying crosslinked siloxane elastomer from about 0.1% to about 8% by weight based on the total weight of the composition;
  d) at least one co-emulsifier from about 0.1% to about 2% by weight based on the total weight of the composition and is selected dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone (and) dimethicone/PEG-10/15 crosspolymer, dimethicone and PEG/PPG-18/18 dimethicone, and combinations thereof.

The water-in-silicone cosmetic compositions of the instant disclosure provide an unexpected and unique occlusive texture with a low friction and high glide that can be applied directly on the skin after dermatology clinic procedures because it spreads very easily and will not irritate or damage the skin further.

It is to be understood that both the foregoing general description and the following detailed description are exemplary and explanatory only, and are not restrictive of the invention.

DETAILED DESCRIPTION OF THE DISCLOSURE

The instant disclosure relates to water-in-silicone cosmetic compositions.

The water-in-silicone cosmetic compositions of the instant disclosure, in their broadest sense, typically include the following:

A) an aqueous phase comprising:
  a) a hydrating agent from about 1% to about 40% by weight based on the total weight of the composition; and
  b) from about 40% to about 80% of water by weight based on the total weight of the composition;

B) a silicone phase having about 18% to about 35% of silicone-containing compounds by weight based on the total weight of the composition, the silicone phase comprising:
  a) at least one silicone polymer;
  b) a film former from about 0.01% to about 4% by weight based on the total weight of the composition;
  c) at least one emulsifying crosslinked siloxane elastomer;
  d) at least one co-emulsifier from about 0.1% to about 2% by weight based on the total weight of the composition and is selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone (and) dimethicone/PEG-10/15 crosspolymer, dimethicone and PEG/PPG-18/18 dimethicone, and combinations thereof.

The water-in-silicone cosmetic compositions of the instant disclosure exhibits a surprisingly occlusive texture. The compositions are particularly interesting in that they are providing a long-lasting sensation and protection, helping to retain moisture. Furthermore, the compositions spread easily, do not irritate skin through friction and do not feel tacky even though there is a high level of glycerin.

As used herein, the term "water-in-silicone" includes a water phase dispersed in an oil phase, where the oil phase is a continuous phase and includes at least one Si emulsifier.

As used herein, the term "occlusive" means serving to close. For example, it may be useful over the opening of a wound to limit exposure of skin to environmental factors.

As used herein, the term "silicone-containing compounds" includes compounds that contain repeating units of siloxane.

Aqueous Phase

Water

The aqueous phase present in the water-in-silicone cosmetic composition includes glycerin, water, and other aqueous phase ingredients. The aqueous phase of the water-in-silicone cosmetic composition may be present in an amount from about 40%, 45%, 50%, 55% to about 55%, 60%, 65%, 70%, or 80% by weight based on the total weight of the composition.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Hydrating Agent

Suitable examples of the hydrating agent, include polyols, for example, glycerol, glycols, such as butylene glycol, propylene glycol, isoprene glycol, dipropylene glycol, hexylene glycol and polyethylene glycols, sorbitol, sugars, such as glucose, and mixtures thereof.

The aqueous phase present in the water-in-silicone cosmetic composition according to the disclosure includes a hydrating agent. The hydrating agent may be present in an amount from about 1%, 2%, 3%, 4%, 4.5%, 5%, 5.5%, 6%, 6.5%, 7%, 8%, 9%, 10%, 12%, 14%, 16% to about 14%, 16%, 18%, 20%, 22%, 24%, 26%, 28%, 30%, 32%, 34%, 35%, 36%, 37%, 38%, 39% or 40% by weight based on the total weight of the composition. In some embodiments, the hydrating agent is glycerin.

Silicone Phase

The silicone phase present in the water-in-silicone cosmetic composition according to the disclosure is having from about 18% to about 40% of silicone-containing compounds by weight based on the total weight of the composition, the silicone phase comprising at least one silicone polymer; a film former from about 0.01% to about 4% by weight based on the total weight of the composition; at least one emulsifying crosslinked siloxane elastomer; at least one co-emulsifier from about 0.1% to about 3% by weight based on the total weight of the composition. In some embodiments, the silicone-containing compounds may be present in an amount from about 18%, 19%, 20%, 21%, 22%, 23%, 24%, 25% to about 25%, 26%, 27%, 28%, 29%, 30%, 35%, or 40% by weight based on the total weight of the composition.

Silicone Polymer

The silicone phase present in the water-in-silicone cosmetic composition according to the disclosure includes at least one silicone polymer. In some embodiments, suitable example of silicone polymers includes, but are not limited to, polydimethylsiloxane (dimethicone), a mixture of dimethicone and dimethiconol, decamethylcyclopentasiloxane (D5), cyclomethicone (mixture of D4, D5 and D6), and combinations thereof.

The silicone polymer may be present in an amount from about 0.01%, 0.02%, 0.03%, 0.04%, 0.05%, 0.1%, 0.5%, 1%, 1.5%, 2%, 2.5%, 3%, 3.5%, 4%, 4.5%, 5%, 6%, 7%, 8%, 9%, 9.5%, 10% to about 9.5%, 10%, 10.5%, 11%, 11.5%, 12%, 13%, 14%, 15%, 15.5%, 16%, 16.5%, 17%, 17.5%, 18%, 18.5%, 19, 19.5%, or 20% by weight based on the total weight of the composition.

Film Former

The silicone phase present in the water-in-silicone cosmetic composition according to the disclosure includes a film former. In some embodiments, suitable example of film formers includes, but are not limited to, Trimethylsiloxysilicate (and) polypropylsilsesquioxane, Acrylates/Polytrimethylsiloxymethacrylate Copolymer, Dimethicone (and) Acrylates/dimethicone copolymer, Polypropylsilsesquioxane, Trimethylsiloxysilicate), Crotonic acid/vinyl C8-12, Isoalkyl Esters/Va/Bis-Vinyldimethicone Crosspolymer.

The film former may be present in an amount from about 0.01%, 0.02%, 0.05%, 0.08%, 0.1%, 0.2% 0.25%, 0.3%, 0.35%, 0.4%, 0.5%, 0.6%, 0.7%, 0.8%, 0.9%, 1%, 1.5% to about 1%, 1.5%, 2%, 2.5%, 3%, 3.5%, or 4% by weight based on the total weight of the composition.

Emulsifying Crosslinked Siloxane Elastomer

The silicone phase present in the water-in-silicone cosmetic composition according to the disclosure includes an emulsifying crosslinked siloxane elastomer. Examples of suitable emulsifying crosslinked siloxane elastomers, include, but are not limited to, substituted or unsubstituted dimethicone/copolyol crosspolymer, dimethicone (and) dimethicone/vinyldimethicone crosspolymer, dimethicone and dimethicone/PEG-10/15 crosspolymers, substituted or unsubstituted dimethicone/polyglyceral crosspolymer, dimethicone and dimethicone/polyglycerin-3 crosspolymer. Such suitable emulsifying crosslinked siloxane elastomers are sold or made, for example, under the names of "KSG-210" a polyether-modified cross polymer with an INCI name of dimethicone (and) dimeticon/PEG-10/15 crosspolymer, and "KSG-710" a polyglycerin-modified crosspolymer with and INCI name of dimethicone (and) dimethicone/polyglycerin-3 crosspolymer, both available from ShinEtsu Silicones of America, Inc. (Akron, Ohio).

The emulsifying crosslinked siloxane elastomer may be present in an amount from about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5% to about 2%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.2%, 4.4%, 4.6%, 4.8%, or 5% by weight based on the total weight of the composition.

Co-Emulsifier

The silicone phase present in the water-in-silicone cosmetic composition according to the disclosure includes at least one co-emulsifier. Suitable examples of co-emulsifiers include polyether substituted linear or branched polysiloxane copolymers. For example, the co-emulsifier can be selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone, dimethicone (and) dimethicone/PEG-10/15 crosspolymer PEG/PPG-18/18 dimethicone, dimethicone/dimethicone crosspolymer, dimethicone (and) dimethicone/polyglycerin-3 crosspolymer and combinations thereof. One preferred co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.). Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

The co-emulsifier may be present in an amount from about 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5% to about 4%, 5%, 5.5%, 6%, 6.5%, 7%, 7.5%, 8%, 8.5%, 9%, 9.5%, 10%, 11%, or 12% by weight based on the total weight of the composition.

Active Ingredient

The aqueous phase or the oil phase, depending on the nature of the active ingredient, includes an active ingredient. The cosmetic composition according to the disclosure includes an active ingredient from about 0.01% to about 5% by weight based on the total weight of the composition. In one embodiment, the active ingredient is capryloyl salicylic acid, adenosine, baicalin, resveratrol, other polyphenols, or combinations thereof. In another embodiment, the active ingredient is an organic or inorganic UV filter, or combination thereof. In some embodiments, the active ingredient is selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof. In one embodiment, one or more actives can be selected from sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

Preservative System

The aqueous phase present in the water-in-silicone cosmetic composition according to the disclosure includes a preservative system at a concentration, by weight of about 0.1% to about 3%, or alternatively about 0.5% to about 2.5% or alternatively about 1% to about 2.0%, based upon weight of the composition. In a preferred embodiment, the preservative system includes preservative system comprises organic acids, parabens, formaldehyde donors, phenol derivatives, quaternary ammoniums, alcohols, isothiazolones, and combinations thereof.

Examples of organic acid preservative systems include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate.

Examples of paraben preservative systems include, but are not limited to, alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben).

Examples of formaldehyde donor preservative systems include, but are not limited to, 1,3-Dimethylol-5,5-dimethylhydantoin (DMDM hydantoin), imidazolidinyl urea, gluteraldehyde, and combinations thereof.

Examples of quaternary ammonium preservative systems include, but are not limited to, benzalkonium chloride, methene ammonium chloride, benzethonium chloride, and combinations thereof.

Examples of alcohol preservative systems include, but are not limited to, ethanol, benzyl alcohol, dichlorobenzyl alcohol, phenoxyethanol, and combinations thereof.

Examples of isothiazolone preservative systems include, but are not limited to, methylchloroisothiazolinone, methylisothiazolinone, and combinations thereof.

Other suitable preservatives for preservative system include, but are not limited to, chloracetamide, triclosan and iodopropynyl butylcarbamate, pyridine derivatives (e.g., pyrithione and zinc pyrithione), chlorphenesin, phenyl mercuric salts, phenoxyethanol, and other know preservative systems.

Fragrance

Fragrance including natural or synthetic odoriferous substances or mixtures thereof may be included in the cosmetic composition of the present disclosure. Use may be made of mixtures of different odoriferous substances which together generate an attractive scent. Natural odoriferous substances are extracts of flowers (lily, lavender, rose, jasmine, neroli or ylang-ylang), stems and leaves (geranium, patchouli, petitgrain), fruits (anis, coriander, caraway, juniper), fruit rinds (bergamot, lemon, orange), roots (mace, angelica, celery, cardamom, costus, iris, thyme), needles and twigs (spruce, fir, pine, mountain pine) and resins and balsams (galbanum, elemi, benzoin, myrrh, frankincense, opoponax). Typical synthetic perfume compounds are products of the esters, ethers, aldehydes, ketones, alcohols and hydrocarbon types. Essential oils of low volatility, which are generally used as flavoring components, are also suitable as fragrances, for example, but not limited to, sage oil, camomile oil, clove oil, balm oil, peppermint oil, cinnamon leaf oil, linden blossom oil, juniper berry oil, vetiver oil, frankincense oil, galbanum oil, labdanum oil and lavandin oil.

The composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, antioxidants (e.g., EDTA, BHT, tocopherol), essential oils, fragrances, dyes, neutralizing or pH-adjusting agents (e.g., citric acid, triethylamine (TEA) and sodium hydroxide), conditioning or softening agents (e.g., panthenol and allantoinin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase).

More exhaustive but non-limiting lists of components useful in the hair care compositions disclosed herein are presented below.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

The following Examples are provided for illustrative purposes only, and are not intended to be limiting.

Example 1: Inventive Examples

TABLE 1

Inventive Examples

| Function | INCI US | Example 1 (inventive) | Example 2 (inventive) |
|---|---|---|---|
| Hydrating agent | GLYCERIN | 15 | 15 |
| Silicone Polymer | DIMETHICONOL | 0.06 | 0.06 |
| Film former | ACRYLATES/ DIMETHICONE COPOLYMER | 0.8 | 0.4 |
| Emulsifying Crosslinked Siloxane elastomer | DIMETHICONE/ POLYGLYCERIN-3 CROSSPOLYMER | 3.625 | |
| Emulsifying Crosslinked Siloxane Elastomer | DIMETHICONE/ PEG-10/15 CROSSPOLYMER | | 1.25 |
| Co-Emulsifier | DIMETHICONE CROSSPOLYMER | | 1.125 |
| Co-Emulsifier | LAURYL PEG-9 POLYDIMETHYL- SILOXYETHYL DIMETHICONE | 0.5 | 0.5 |
| Co-emulsifer | DIMETHICONE/VINYL DIMETHICONE CROSSPOLYMER | 3.24 | |
| Co-emulsifier | DIMETHICONE/VINYL DIMETHICONE CROSSPOLYMER | | 1.05 |
| Total Silicones | | 23.28 | 23 |
| Active | SODIUM CITRATE | 0.5 | 0.5 |
| Active | CITRIC ACID | 0.35 | 0.2 |
| Preservative | PHENOXYETHANOL | 0.6 | 0.6 |
| Solvent | CAPRYLYL GLYCOL | 0.3 | 0.3 |
| Vitamin | PANTHENOL | 5 | 5 |
| Q.S. | WATER | 48.25 | 53.9 |

The Inventive Examples in Table 1 were prepared according to the procedure as follows: All silicones were mixed using a prop blade. Glycerin was slowly added to the silicone phase by the use of a prop blade as well. While this phase was mixing, the water phase was heated to solubilize all aqueous soluble ingredients and cooled to room temperature. Once cool, that phase was added slowly to the silicone glycerin phase by use of prop blade as well.

The examples in Table 1 include inventive examples having a long lasting occlusive barrier that hydrates, protects and helps heal the skin. The inventive examples also provide a water-releasing effect.

Despite the presence of a high percentage of glycerin, the formulas do not exhibit a tacky feel that occurs usually with such a high level of glycerin.

Example 2: Properties of the Inventive Examples

TABLE 2

Inventive and Comparative Examples

| Ingredients | Example 2 (inventive) | Example 3 (Comparative) | Example 4 (Comparative) |
|---|---|---|---|
| Silicone % | 23 | 13 | 13.07 |
| Film Former | 0.4 | 0 | 0 |
| Glycerin % | 15 | 15 | 64.39 |
| Water % | 53.9 | 55.4 | 64.4 |

TABLE 3

Properties Results

| Property tested | Results | Example 2 (Inventive) | Example 3 (Comparative) | Example 4 (Comparative) |
|---|---|---|---|---|
| Water Break | | moderate | moderate | extreme |
| Occlusive feel | Maintains feel after 1 min | yes | yes | yes |
| | Maintains feel after 2 mins | yes | yes | yes |
| | Maintains feel after 3 mins | yes | yes | no |
| | Maintains feel after 5 mins | yes | yes | no |
| | Maintains feel after 10 mins | yes | yes | no |
| | Maintains feel after 30 mins | yes | no | no |
| | Maintains feel after 45 mins | yes | no | no |
| | Maintains feel after 1 hr. | yes | no | no |

In Table 3, two properties were tested, the water-break and the occlusive feel.

The Water Break Test

The water break property is unique to a water-in-silicone emulsion. When the formula is spread on the skin, the water is forced out of the emulsion, thus resulting in a water break feel. This water break can also be visualized as water droplets form on the skin after rubbing. The water break test was performed to evaluate the perceivable level of water breaking from the formula. By rubbing the formula on the skin, both a visual and sensorial level of water break were recorded for 10 different individuals.

Occlusive Feel Test

The occlusive feel of the formula was performed to evaluate how long the formula maintains an occlusive layer on the skin. Formulas were weighed and spread on the forearm and left without interference for 1 hour. After each time point, the occlusive layer on the skin was evaluated by both a visual and sensorial analysis of 10 different individuals. The time in which the formula was no longer occlusive was recorded.

The water-in-silicone emulsion of inventive Example 2 included about 23% of silicones containing compounds, about 0.4% of film former, and 15% of glycerin. The emulsion formed in Example 2 released some droplets upon rubbing. It is what is called "water break" and was stated to be moderate. Furthermore, the occlusive feel of the water-in-silicone emulsion of Example 2 was tested over time after application on the skin. The occlusive feel was detected 1 min after the application on the skin and was maintained even after one hour.

The water-in-silicone emulsion of comparative Example 3 included about 13% of silicones containing compounds, no film former, and 15% of glycerin. The emulsion formed in Example 3 released some droplets upon rubbing. It is what is called "water break" and was stated to be moderate. Furthermore, the occlusive feel of the water-in-silicone emulsion of Example 3 was tested over time after application on the skin. The occlusive feel was detected 1 min after the application on the skin and was still observed 10 min after application. However, the occlusive feel disappeared after 30 min of application and became insignificant.

The water-in-silicone emulsion of comparative Example 4 included about 13.8% of silicones containing compounds, no film former, and 15% of glycerin. The emulsion formed in Example 4 released a lot of droplets upon rubbing. It is what is called "water break" and was stated to be extreme. Furthermore, the occlusive feel of the water-in-silicone emulsion of Example 4 was tested over time after application on the skin. The occlusive feel was detected and was maintained, but only after 2 min of application on the skin. After 2 min, the emulsion was absorbed and the occlusive feel was not felt anymore on the skin.

The results shown in Table 3 demonstrate that the association of a high percentage of silicones with a certain amount of film former (i.e. Example 2) improved the texture of the water-in-silicone emulsion and gave the emulsion a feeling of long lasting protective formula that glides very easily and has a low friction.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A water-in-silicone cosmetic composition in the form of an liquid emulsion, the composition comprising:
    A) an aqueous phase comprising:
        a) glycerin from about 10% to about 40% by weight based on the total weight of the composition;
        b) from about 40% to about 80% of water by weight based on the total weight of the composition;
    B) a silicone phase having from about 18% to about 40% of silicone-containing compounds by weight based on the total weight of the composition, the silicone phase comprising:
        a) at least one silicone polymer;
        b) a film former from about 0.1% to about 2% by weight based on the total weight of the composition and is selected from the group consisting of Trimethylsiloxysilicate (and) polypropylsilsesquioxane, Acrylates/Polytrimethylsiloxymethacrylate Copolymer, Dimethicone (and) Acrylates/dimethicone copolymer, Polypropylsilsesquioxane, Trimethylsiloxysilicate), Crotonic acid/vinyl C8-12, Isoalkyl Esters/Va/Bis-Vinyldimethicone Crosspolymer;
        c) at least one emulsifying crosslinked siloxane elastomer;
        d) at least one co-emulsifier from about 0.1% to about 3% by weight based on the total weight of the composition; and
            wherein the water-in-silicone cosmetic composition in the form of an liquid emulsion is applied directly onto the skin.

2. The water-in-silicone cosmetic composition of claim 1, wherein the glycerin is present from about 10 to about 35% by weight based on the total weight of the composition.

3. The water-in-silicone cosmetic composition of claim 1, wherein the at least one silicone polymer is selected from the group consisting of dimethicone, a mixture of dimethicone and dimethiconol, decamethylcyclopentasiloxane, cyclomethicone, and combinations thereof.

4. The water-in-silicone cosmetic composition of claim 1, wherein the at least one silicone polymer is from about 0.01% to about 20% by weight based on the total weight of the composition.

5. The water-in-silicone cosmetic composition of claim 4, wherein the at least one silicone polymer is from about 0.1% to about 15% by weight based on the total weight of the composition.

6. The water-in-silicone cosmetic composition of claim 1, wherein the film former is from about 0.2% to about 2% by weight based on the total weight of the composition.

7. The water-in-silicone cosmetic composition of claim 6, wherein the film former is from about 0.3% to about 2% by weight based on the total weight of the composition.

8. The water-in-silicone cosmetic composition of claim 1, wherein the at least one emulsifying crosslinked siloxane elastomer comprises a substituted or unsubstituted dimethicone/copolyol crosspolymer.

9. The water-in-silicone cosmetic composition of claim 8, wherein the at least one emulsifying crosslinked siloxane elastomer is selected from dimethicone (and) dimethicone/vinyldimethicone crosspolymer, dimethicone (and) dimethicone/PEG-10/15 crosspolymer.

10. The water-in-silicone cosmetic composition of claim 9, wherein the emulsifying crosslinked siloxane elastomer is dimethicone/PEG-10/15 crosspolymer.

11. The water-in-silicone cosmetic composition of claim 1, wherein the at least one emulsifying crosslinked siloxane elastomer comprises a substituted or unsubstituted dimethicone/polygyceral crosspolymer.

12. The water-in-silicone cosmetic composition of claim 11, wherein the emulsifying crosslinked siloxane elastomer is dimethicone/polyglycerine-3 crosspolymer.

13. The water-in-silicone cosmetic composition of claim 1, wherein the at least one co-emulsifier is selected from polyether substituted linear and branched polysiloxane copolymers.

14. The water-in-silicone cosmetic composition of claim 13, wherein the at least one co-emulsifier is selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone, dimethicone (and) dimethicone/PEG-10/15 crosspolymer PEG/PPG-18/18 dimethicone, dimethicone/dimethicone crosspolymer, dimethicone (and) dimethicone/polyglycerin-3 crosspolymer and combinations thereof.

15. The water-in-silicone cosmetic composition of claim 14, wherein the at least one co-emulsifier is lauryl PEG-9 Polydimethylsiloxyethyldimethicone.

16. The water-in-silicone cosmetic composition of claim 1, wherein the at least one co-emulsifier is present in an amount from about 0.01% to about 12% by weight based on the total weight of the composition.

17. The water-in-silicone cosmetic composition of claim 1, wherein the silicone-containing compounds are present from about 20% to about 35% by weight based on the total weight of the composition.

18. The water-in-silicone cosmetic composition of claim 1, further comprising one or more additional components selected from the group consisting of actives selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

19. The water-in-silicone cosmetic composition of claim 18, further comprising one or more actives selected from the group consisting of sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

20. A water-in-silicone cosmetic composition in the form of an liquid emulsion, the composition comprising:
A) an aqueous phase comprising:
  a) glycerin from about 6% to about 35% by weight based on the total weight of the composition; and
  b) water from about 50% to about 70% by weight based on the total weight of the composition;
B) a silicone phase having from about 20% to about 38% of silicone-containing compounds by weight based on the total weight of the composition, the silicone phase comprising:
  a) at least one silicone polymer from about 0.01% to about 20% by weight based on the total weight of the composition;
  b) a film former from about 0.2% to about 3% by weight based on the total weight of the composition and is selected from the group consisting of Trimethylsiloxysilicate (and) polypropylsilsesquioxane, Acrylates/Polytrimethylsiloxymethacrylate Copolymer, Dimethicone (and) Acrylates/dimethicone copolymer, Polypropylsilsesquioxane, Trimethylsiloxysilicate), Crotonic acid/vinyl C8-12, Isoalkyl Esters/Va/Bis-Vinyldimethicone Crosspolymer;
  c) at least one emulsifying crosslinked siloxane elastomer from about 0.1% to about 8% by weight based on the total weight of the composition;
  d) at least one co-emulsifier from about 0.1% to about 2% by weight based on the total weight of the composition and is selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone (and) dimethicone/PEG-10/15 crosspolymer, dimethicone and PEG/PPG-18/18 dimethicone, and combinations thereof, and
  wherein the water-in-silicone cosmetic composition in the form of an liquid emulsion is applied directly onto the skin.

* * * * *